US008119151B2

(12) United States Patent
Heidner et al.

(10) Patent No.: US 8,119,151 B2
(45) Date of Patent: Feb. 21, 2012

(54) SPREAD COATING A MEDICAL DEVICE

(75) Inventors: Matt Heidner, Maple Grove, MN (US); Tim J. Mickley, Elk River, MN (US); Michael S. Owens, Richfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 978 days.

(21) Appl. No.: 12/106,012

(22) Filed: Apr. 18, 2008

(65) Prior Publication Data

US 2008/0260936 A1 Oct. 23, 2008

Related U.S. Application Data

(60) Provisional application No. 60/912,939, filed on Apr. 20, 2007.

(51) Int. Cl.
*A61F 2/86* (2006.01)

(52) U.S. Cl. ....................................... 424/423; 427/2.24

(58) Field of Classification Search .................. 424/423; 427/2.24
See application file for complete search history.

(56) References Cited

U.S. PATENT DOCUMENTS 4,102,301 A 7/1978 Reade et al.
6,395,326 B1 5/2002 Castro et al.
6,984,411 B2 1/2006 Palasis et al.
7,060,319 B2 6/2006 Fredrickson
2005/0074544 A1 4/2005 Pacetti et al.
2005/0100654 A1 5/2005 Su et al.
2006/0121081 A1 * 6/2006 Labrecque et al. ........... 424/423
2007/0032856 A1 * 2/2007 Limon ......................... 623/1.15
2007/0110888 A1 5/2007 Radhakrishnan et al.

OTHER PUBLICATIONS

International Search Report with Written Opinion (PCT/US2008/060838), dated Dec. 10, 2008.

* cited by examiner

*Primary Examiner* — John Hardee
(74) *Attorney, Agent, or Firm* — Vidas, Arrett & Steinkraus, P.A.

(57) ABSTRACT

The present invention is directed to methods, systems, devices, and kits for coating portions of a medical device or other work piece as well as to medical devices that have themselves been coated in accord with the invention. Under methods of the invention, portions of a medical device may be selectively coated. The method may include providing a medical device, an applicator, and a spreader. A layer of coating having a thickness may then be applied to a target surface of the medical device with the applicator. When the coating is applied, the spreader can be positioned in contact with the coating to reduce the coating thickness by spreading the coating over a larger surface area of the target surface.

19 Claims, 5 Drawing Sheets

SPREAD COATING A MEDICAL DEVICE

CROSS REFERENCE TO RELATED APPLICATION

The present application claims priority to U.S. provisional application Ser. No. 60/912,939, filed Apr. 20, 2007, the disclosure of which is incorporated herein by reference in its entirety.

TECHNICAL FIELD

The present invention generally relates to methods for selectively coating medical devices. More specifically, the present invention relates to medical devices, such as expandable stents, self-expanding stents, and vena-cava filters, and methods for coating these devices, wherein a coating is applied to the medical device and then spread on one or more accessible surfaces of the device.

BACKGROUND

Coating medical devices is an often repeated procedure in contemporary manufacturing. Medical devices may be coated by methods that include spray coating, dip coating and roll coating. During each of these procedures coating is applied to the medical device and is then allowed to dry or cure prior to the medical device being used for an intended purpose.

When the medical device is formed partially or completely out of lattice struts or some other open framework, each of the faces of these struts or framework may be exposed to coating during the coating methods listed above.

In some cases, when the medical device being coated is a stent, all faces of the struts that comprise the stent may be coated when using the coating systems identified above. For example, when dip coating is used, each face of the stent struts will be exposed to the coating and thereby coated. This coating will remain when the stent is removed from the dip and will dry on surfaces of the struts without further intervention. Coating may even remain in the spaces between the struts after the coating has been applied to the workpiece. This phenomenon is sometimes called "webbing." Here, not only are the individual struts covered, but some or all of the spaces between the struts are spanned by the coating as well.

BRIEF DESCRIPTION

The present invention is directed to methods, systems, devices, and kits, wherein a coating is applied to an accessible surface of a medical device and then subsequently spread. The coating may be spread to other areas of the medical device not in contact with the coating when it is first applied. The coating may also be spread to reduce the thickness of the coating on the medical device and to change its coverage area. The coating may be spread for other reasons. The coating may be applied by various applicators and it may be spread by various spreaders as well. The applicators employed may include hand-held devices and computer controlled devices. Likewise, the spreaders may themselves be hand-operated and may also be more automated. The coating being applied may include a therapeutic agent and it may be applied directly to the medical device as well to a coating already present on a medical device. Portions of the coating may be dried during the coating process while other portions remain wet or not dried.

The invention may be embodied through numerous devices, systems, methods, and kits. The following detailed description, which, when taken in conjunction with the annexed drawings, discloses examples of the invention. Other embodiments, which incorporate some or all of the features as taught herein, mixing and drawing from the various descriptions, are also possible.

BRIEF DESCRIPTION OF THE DRAWINGS

Referring to the drawings, which form a part of this disclosure.

DETAILED DESCRIPTION

The present invention regards coating one or more accessible surfaces of a medical device while not coating other surfaces of the medical device. In some embodiments this may include coating the outside or side surfaces of the medical device while not coating the inside surfaces of the medical device. In some instances this may include coating the inside surfaces of the device. By selectively coating in this fashion the amount of coating resident on the medical device may be reduced. This can be useful when the amount of coating is metered or otherwise is of interest. For example, if the medical device is a stent and the coating contains therapeutic agent a reduction in coating may allow the therapeutic agent, to be delivered in a more targeted fashion after the stent is implanted at a target site. The controlled application of therapeutic may also improve the efficiency of the process and reduce the amount of lost or wasted therapeutic.

The selective coating of a medical device may be accomplished with an applicator and spreader. An applicator may apply a layer of coating onto an accessible surface of a strut of a lattice portion of a stent. During or after the coating is the applied, a spreader, such as a roller, may be used to spread the coating on the accessible surfaces of the stent. The spreader may remove coating during this process and may also be in communication with a coating reservoir to deliver additional coating if desired. Each of the medical device, the applicator, and the spreader may be movable relative to each other to facilitate the coating of one or more surfaces of the work piece.

Figure 1D:
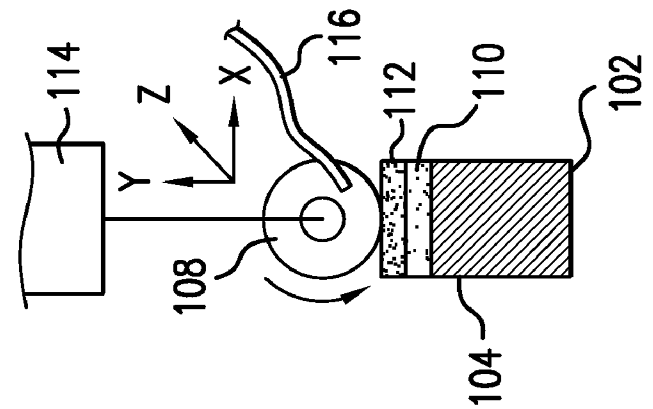
FIG. 1*d* shows the spreader of FIG. 1*b* in contact with coating on the strut and also applying additional coating.
Figure 1C:
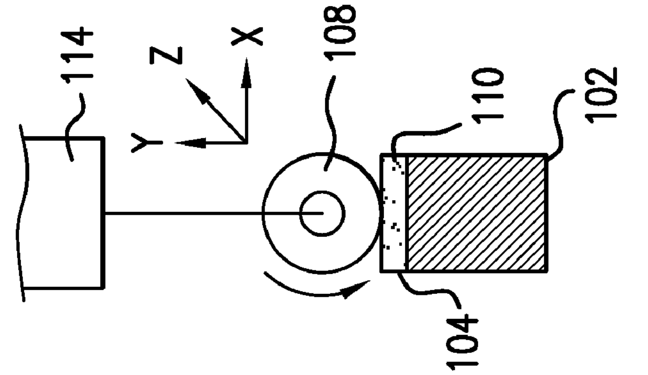
FIG. 1*c* shows the spreader of FIG. 1*b* in contact with coating on the strut.
Figure 1B:
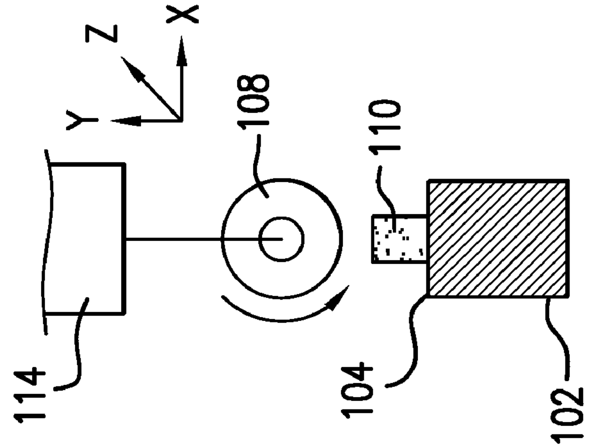
FIG. 1*b* shows a spreader positioned above the coated strut of FIG. 1*a* in accord with the present invention.
Figure 1A:
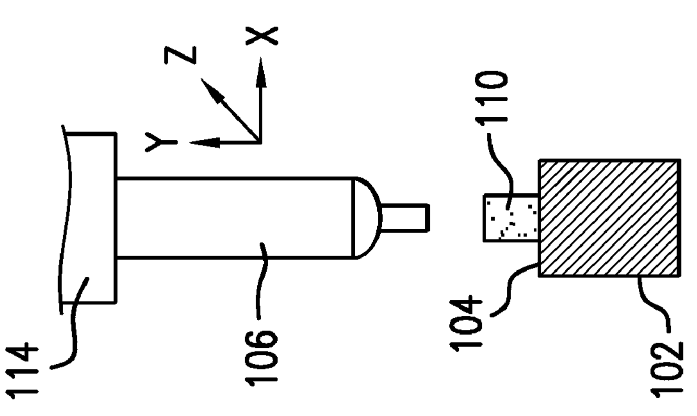
FIG. 1*a* shows an applicator coating a strut of a medical device as may be employed in accord with the present invention.
Figure 6A:
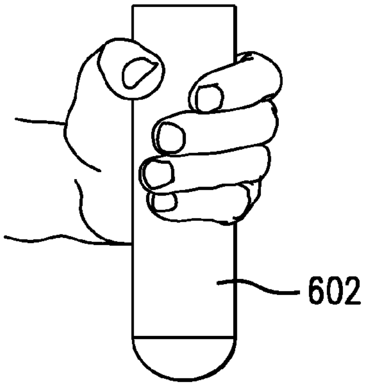
FIG. 6*a* shows a ball-point applicator which may be used in accord with the present invention.
Figure 6B:
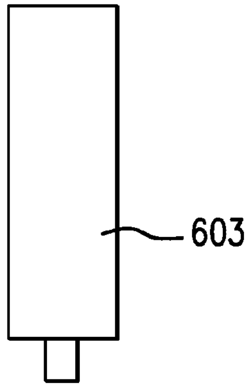
FIG. 6*b* shows a felt-tip applicator which may be used in accord with the present invention.
Figure 6C:
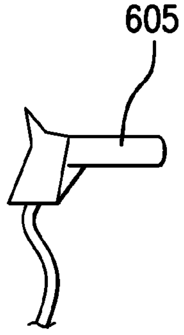
FIG. 6*c* shows a paint gun which may be used in accord with the present invention.

A system for coating an accessible outer surface 104 of a strut 102 of a lattice portion of a stent in accord with the present invention is shown in FIGS. 1*a-d*. There, a coating system is shown having an applicator 106 and a spreader 108. The applicator 106 visible in FIG. 1*a* is a micro-scale dispenser, however, any suitable applicator 106 may be used including, but not limited to ball point applicators, felt-tip applicators, and paint guns, which are shown in FIGS. 6*a*-6*c*. In FIG. 1*a*, the micro-scale dispenser 106 may be a fluid dispensing system which is configured to place coating 110 onto the strut 102. For example, the micro-scale dispenser 106 may be coordinated with the movement of the strut 102 to dispense coating 110 on a unique external pattern of the work piece, in this instance a stent, within precise dimensions.

Although in the preceding examples, the applicators 106 are shown connected to a machine tool 114 component, the applicators 106 may also be hand-held.

Figure 7A:
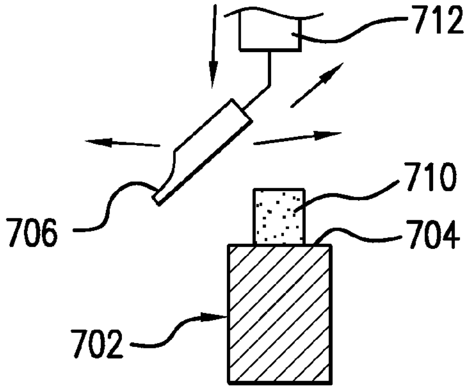
FIG. 7*a* shows a blade which may be used in accord with the present invention positioned prior to contacting the coating on a strut.
Figure 7B:
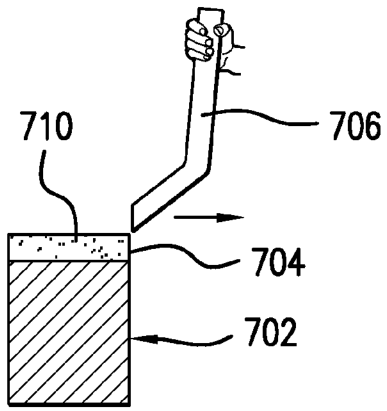
FIG. 7*b* shows a blade which may be used in accord with the present invention.

The spreader 108 shown in FIG. 1*b* is a roller, however, any suitable spreader device 108 for regulating coating may be used including, but not limited to rods, pins, straight edges, serrated edges, coils, which are not shown, and blades which are shown FIG. 7*a*-7*b*. In the example, the roller is about the same size as the width of the outer surface 104 of the strut 102. In some instances, the spreader 108 may be hand-held, and in other instances, the spreader 108 may be connected to a machine tool 114. For example, in FIGS. 1*b*-1*d*, the roller is connected to a conventional machine tool 114 configured to move the roller in the x, y, and z planes.

As seen in FIG. 1*a*, the applicator 106 may apply a layer of coating 110, such as a bead, having a thickness. In this example, a bead of coating 110 is applied to accessible outer surface 104 of a strut 102 of a lattice portion of the medical device. Then, as shown in FIGS. 1*b-c*, once the coating 110 is applied, the spreader may be positioned in contact with the coating 110 to apply pressure to spread the coating 110 over a larger surface area of the outer surface 104 of the stent. In so doing the original thickness of the bead of coating 110 dispensed from the applicator 106 may be reduced through the application of pressure by the spreader. The spreader shown in the figures may be moved along any desired axis or in any direction.

FIG. 1*d* shows another step that may be used in accord with embodiments of the present invention. In this example, the spreader illustrated may, in addition to being able to apply pressure to reduce coating thickness, also be in fluid communication 116 with a coating reservoir (not shown) to apply additional coating 112 during the pressing step. The sequence of FIGS. 1*a*-1*d* may be reordered, added, removed, or combined in accord with the teachings of the invention. The sequence may also be modified in other ways, such as by repeating the steps in continuous fashion.

Various dispensing process parameters may also be controlled to extend control over the thickness and position of the coating 110 placed on the medical device. For example, coating solution viscosity and the amount of pressure the spreader applies can each be varied to adjust the resulting thickness and position of coating 110, 112 resident on the medical device after it has been applied and spread.

Figure 2:
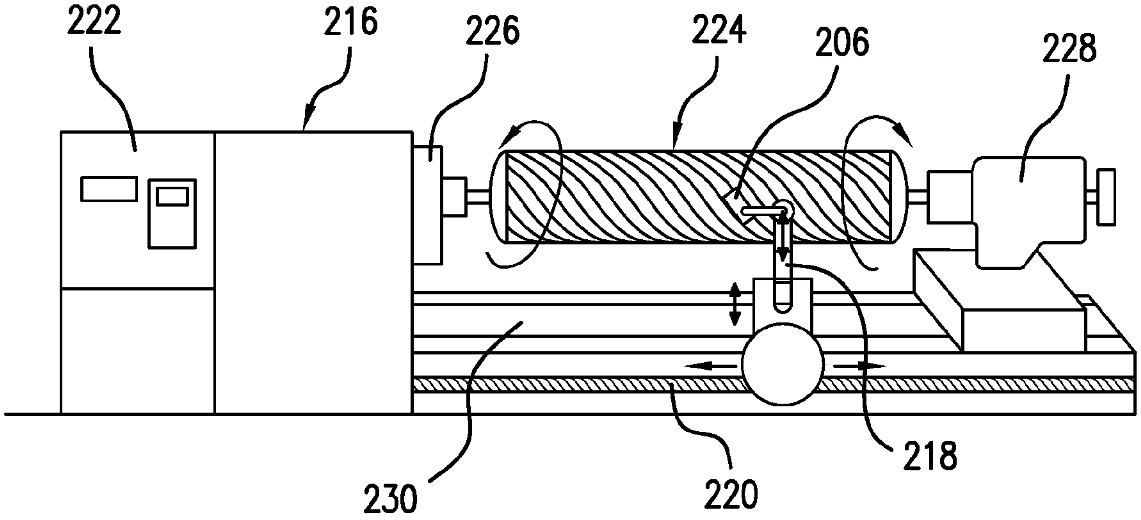
FIG. 2 shows a medical device positioned on a machine tool applicator as may be employed in accord with the present invention.

FIG. 2 shows a machine tool 216 that may be employed in accord with embodiments of the present invention. In the example, a lathe is shown, however, any suitable machine tool 216 for holding, positioning, and rotating medical devices may be used. The applicator 206 may be fixed to a moveable mounting referred to as a tool post 218. The tool post 218 is operated by lead screws 220 which together can accurately position the applicator 206 in a variety of planes (i.e., x, y, and z planes). The tool post 218 may be driven manually and may be driven automatically in coordination with a computer 222.

As is evident in FIG. 2, the medical device 224 may be rotatably supported between a pair of points called centers. One centre is located on a head stock 226. The head stock 226 includes a chuck for mounting one end of the medical device 224. The other centre is mounted on a tail stock 228. The tail stock 228 is slidable towards and away from the head stock 226 along a lathe bed 230. Once rotatably mounted, the tool post 218 may be advanced along the lathe bed 230 so that the applicator 206 can apply coating, such as to the exposed surface of the strut of the lattice portion of a stent. The head and tail stocks 226, 228 allow for rotational movement of the medical device 224. Likewise, as noted above, the tool post 218 allows the applicator 206 to move back and forth along the medical device 224 in the x, y, and z planes. Consequently, the entire surface of the medical device 224 is accessible.

Although the previous example shows a lathe, any suitable machine tool 216 may be used. A machine tool 216 may include any powered mechanical device used to fabricate or assemble components, such as metal stock. For example, a milling machine may also be used.

In accord with the embodiments of the invention, the machine tool 216 may be operated by computer numerical control (CNC). CNC refers to a computer 222 controller system which reads G-code instructions which drive the machine tool. The controller system is programmable with instructions or other retained data which may be unique to each medical device 224 to be coated and may account for the unique external pattern and precise dimensions of each medical device 224 to be coated. The controller system may also hold unique instruction sets for many different medical devices 224.

A medical device 224, such as stent in this embodiment, may be rotated by the machine tool 216 to expose different sides of the medical device 224 to the applicator 206. As described herein, the applicator 206 may also be moved in the x, y, and z directions. Consequently, through the coordinated movement of the medical device 224 and/or the applicator 206, in conjunction with the displacement of coating, all target portions of the medical device 224 may be exposed to and coated by the applicator 206.

Figure 3A:
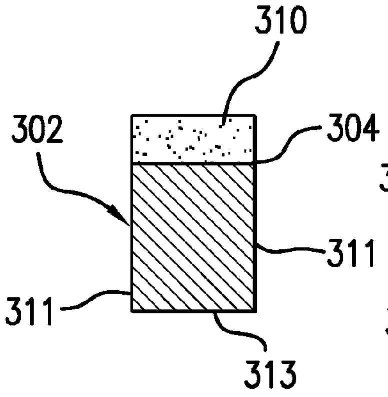
FIG. 3*a* is a cross-sectional view of a portion of a coated strut from a medical device that has been coated in accord with the present invention.

FIG. 3*a* is a side sectional view of a strut 302 of a stent which may be coated in accord with the present invention. The strut 302 in FIG. 3*a* has an inner surface 313, an outer surface 304, and two cut faces 311. Also shown on the strut 302 is a coating 310. As can be seen, the coating 310, covers only one face of the strut 302.

Figure 3B:
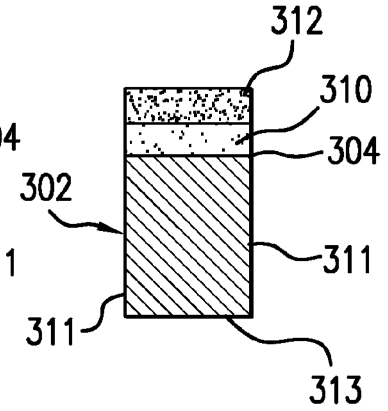
FIG. 3*b* is a cross-sectional view showing the coated strut of FIG. 3*a* after a second coating has been applied as may be employed in accord with the present invention.

FIG. 3*b* shows another example of how a coating 310 may be applied in accord with the invention. In FIG. 3*b*, a first coating 310 and a second coating 312 have been applied to the strut 302. As can be seen, the first coating 310 is in contact with the strut 302 while the second coating 312 is in contact with the first coating 310 and further covers the outer surface 304 of the strut 302. This second coating 312 may be applied in accord with the processes and methods of the present invention. It may also be applied with different methods and processes. In this example, as well as with the others described herein, if a second coating is employed this coating may comprise the same materials as the first coating and it may differ from the materials used for the first coating. In still other examples the coating may be applied in other patterns as well. For example, it may be applied to opposing cut faces and not the outer surface, likewise it may be applied to both cut faces and the outer surface. In an exemplary embodiment, the outer surface is coated and the two cut faces as well as the inner surface are not.

Figure 3C:
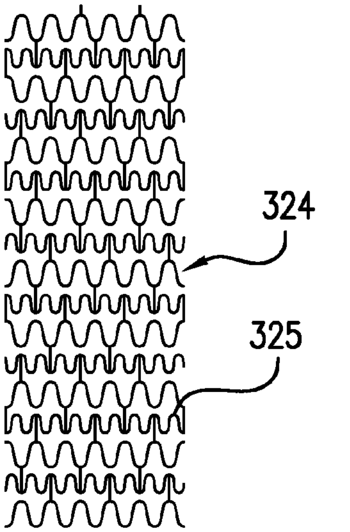
FIG. 3*c* is a side-view of a stent, which is a medical device that may be coated in accord with the present invention.

FIG. 3*c* is a side view of an implantable stent 324 including a lattice portion 325 that may be coated in accord with the invention. The stent 324 may be porous or have portions thereof that are porous. The struts 302 shown in FIGS. 3*a* and 3*b* are struts 302 that may comprise and make up this stent 324. While the medical device shown in these initial figures is a stent 324, many other medical devices may be coated in accord with the invention. For example, other medical devices that may be coated include filters (e.g., vena cava filters), stent grafts, vascular grafts, intraluminal paving systems, implants and other devices used in connection with drug-loaded coatings and treatments. Likewise, the medical device may not be an implantable medical device but may, instead, be another medical device that needs to be coated only on certain pre-selected surfaces. In some instances these medical devices may be made from conductive materials and in other instances they may not be. For example, they may be made from polymers or ceramics.

The medical implants themselves may be self-expanding, mechanically expandable, or hybrid implants which may have both self-expanding and mechanically expandable characteristics. Mechanical or expandable medical devices may aid in traversing the narrower peripheral arteries and allow for expansion to the appropriate size/geometry when the targeted vessel lumen is reached.

Figure 4:
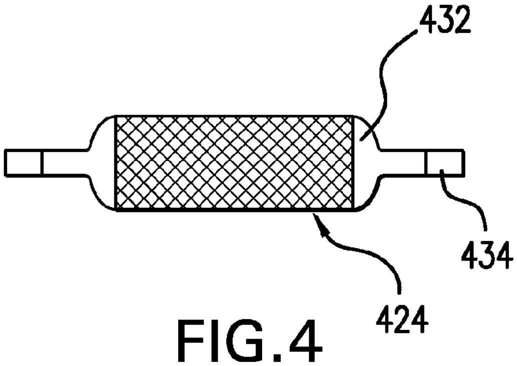
FIG. 4 shows a medical device positioned on a mandrel which may be employed in accord with the present invention.

FIG. 4 shows another method step which may be used in accord with embodiments of the present invention. In FIG. 4, a medical device 424 is positioned on a mandrel 432. The mandrel 432 may be any suitable device such as a inflatable balloon or sheathing comprised of masking material to prevent non-target surfaces of the medical device from coating. In the example, the medical device 424 is positioned over the mandrel 432. Therefore, the inner surfaces and at least portions of the cut faces of the medical device 424 are prevented from being coated by the applicator during the coating process. Additionally, the ends of the mandrel 432 may also be provided with rigid support elements 434, for example, to rotatably support the device within the head and tail stocks of the machine tool described herein. In other examples, which are not shown, the medical device may be connected to machine tools and work holders in a variety of different ways. For example, the medical device may be configured for direct mounting with the machine tool.

Figure 5:
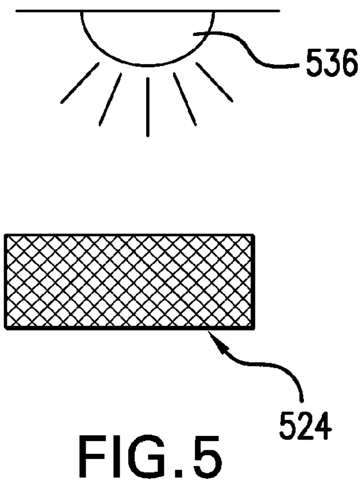
FIG. 5 shows a side-view of a dryer which may be used to dry the medical device during the coating process in accord with the present invention.

Another step in a method embodying the invention may include drying the medical device during the coating process or after the coating process is complete. For example, as shown in FIG. 5, the coated medical device 524 may be positioned proximate to a heating element 536 to partially dry the medical device 524 after the applicator delivers coating. In this example, the heating element 536 is an infrared heating lamp, however, any suitable heating element 536 may be used. In other instances, such as after the metering device is used or after the coating process is complete, heat may be applied to the medical device 524 to dry coating located thereon.

FIGS. 6*a*-6*c* show embodiments of the applicator of FIGS. 1*a* and 2. FIG. 6*a* shows an example of a hand held ball point applicator 602 that may be employed in accord with the embodiments of the present invention. The ball point applicator 602 may be similar in size and shape to a pen or pencil. The ball point applicator 602 has an internal chamber filled with coating which may be dispensed at the tip during use by the rolling action of a suitable metal or plastic sphere.

FIG. 6*b* illustrates an example in which a marker type applicator 603 is used. The marker type applicator 603 has its own coating source and the tip is made of porous material, which in the instant case is felt.

In the example of FIG. 6*c* a paint gun type applicator 605 is shown. In this instance, the single action of depressing the trigger releases a fixed ratio of coating to the air. Through proper positioning of the nozzle of the paint gun, coating may be directed towards the target surface of the work piece.

In all of the embodiments described, the applicators may be positioned on or with respect to any suitable machine tool, and, may also be hand held. Furthermore, although the preceding examples illustrate various applicators, the embodiments of the present invention are not limited thereto and alternative applicators may also fall within the scope of the invention.

FIGS. 7*a*-*b* and 8*a*-8*b* show embodiments of the spreader of FIGS. 1*b*-*d*. FIG. 7*a* shows a bead of coating 710 which may be dispensed from the applicator and transferred to an exposed outer surface 704 of the strut 702 of a lattice portion of the stent. The coating 710 may then be smoothed, squeegeed, or otherwise spread over the target surface by the blade 706. The blade 706 may be moved in any desired direction or directions and may be attached to machine tool component 712. For example, in FIG. 7*a* the blade 706 is moving downward to put pressure on the coating 710. Consequently, the coating 710 spreads out. Accordingly, the blade 706 may then be moved longitudinally to remove coating 710. The amount of coating 710 remaining on the medical device may depend upon the depth and movement of the blade 706. The blade 706 may be adjusted to control the resulting film thickness as desired.

FIG. 7*b* shows another example in which a hand held blade 706 may be used to further regulate coating located on an exposed surface outer surface 704 of the strut 702 of a lattice portion of the stent, such as the strut of FIG. 1*c*. Although, the blade 706 shown is hand held, as with previous examples, the blade 706 may also be attached to a machine tool component.

Figure 8A:
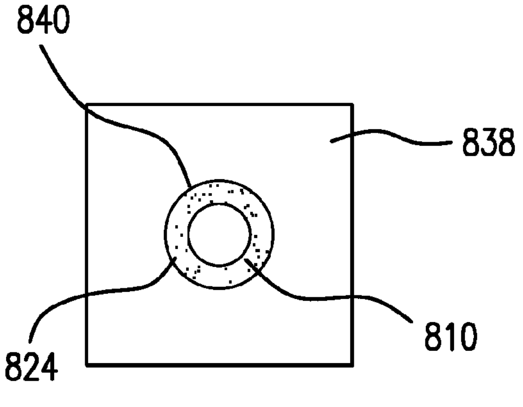
FIG. 8*a* is a front-view of a plate having a reducing orifice as may be employed in accord with the present invention.
Figure 8B:
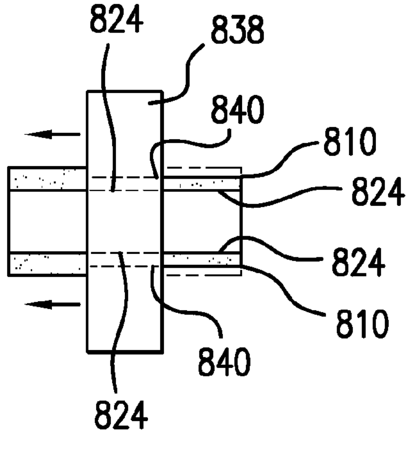
FIG. 8*b* shows the plate of FIG. 8*a* moving over a medical device to reduce a coating thickness.

FIGS. 8*a* and 8*b* show a coated stent 824 and a plate 838 having a reducing orifice 840 which may be employed in accord with the embodiments of the present invention including those in FIGS. 1*a*-1*d*. The reducing orifice 840 may also be used as a spreader to assist in regulating a thickness of coating 810.

In this example, the plate 838 and reducing orifice 840 may move along the stent in a longitudinal direction, however, any suitable arrangement may be used. For example, the stent 824 may be moved through a stationary reducing orifice 840. As the reducing orifice 840 moves over the stent 824, the thickness of the coating 810 reduces slightly. As each portion of the stent 824 exits the reducing orifice 840, pressure is applied to the coating 810 and the coating thickness of the stent 824 may be reduced a predetermined distance. Since the target surface of the coating 810 may be held in about the same radial position relative to the reducing orifice 840, the reducing orifice 840 may eliminate irregularities that may arise when coating the target surface of the stent 824. For instance, variations forming on the target surface may be reduced.

In all of the embodiments described, the spreader may be positioned on or with respect to any suitable machine tool, and, may also be hand-held. Furthermore, although the previous examples illustrate various spreaders, the embodiments of the present invention are not limited thereto and alternative spreaders may also fall within the scope of the invention.

Figure 9:
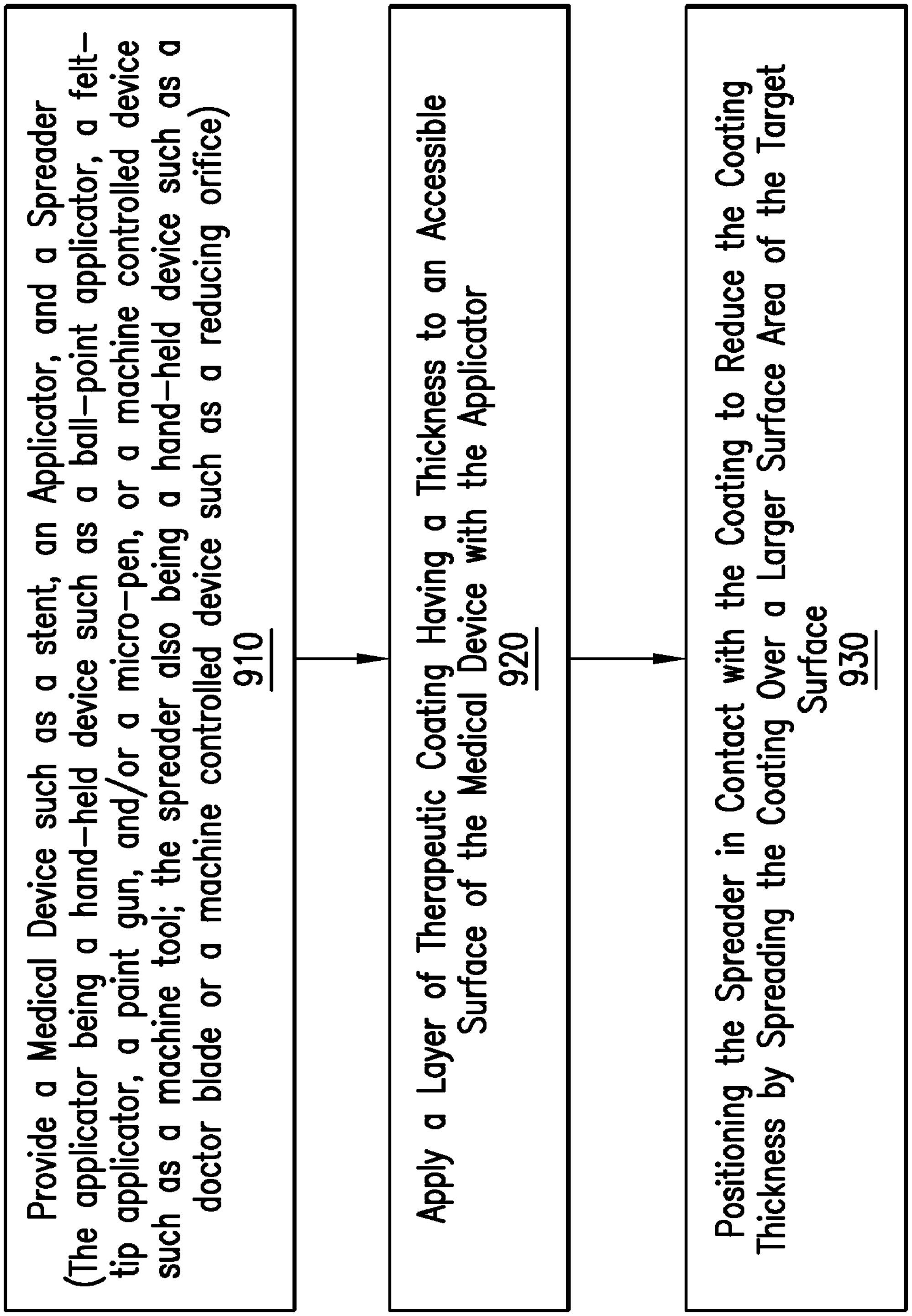
FIG. 9 shows a flow-chart illustrating method steps that may be employed with embodiments of the present invention.

FIG. 9 shows a flow chart including method steps that may be employed with embodiments of the present invention to coat a target surface of a work piece. In the example of FIG. 9, step 910 may include providing a work piece, an applicator, and a spreader. Step 920 may include applying a layer of coating having a thickness to a target surface of the work piece with the applicator. Step 930 may include positioning the spreader in contact with the coating to reduce the coating thickness by spreading the coating over a larger surface area of the target surface. In embodiments, not shown, the sequence of steps may be reordered and steps may be added or removed. The steps may also be modified to include and use other devices described herein. Further, the steps may be repeated in continuous fashion.

While various embodiments have been described, other embodiments are plausible. It should be understood that the foregoing descriptions of various examples of the applicator and spreader are not intended to be limiting, and any number of modifications, combinations, and alternatives of the examples may be employed to facilitate the effectiveness of the coating of target surfaces of a medical device.

The coating, in accord with the embodiments of the present invention, may comprise a polymeric and or therapeutic agent formed, for example, by admixing a drug agent with a liquid polymer, in the absence of a solvent, to form a liquid polymer/drug agent mixture. A suitable list of drugs and/or polymer combinations is listed below. The term “therapeutic agent” as used herein includes one or more “therapeutic agents” or “drugs.” The terms “therapeutic agents” or “drugs” can be used interchangeably herein and include pharmaceutically active compounds, nucleic acids with and without carrier vectors such as lipids, compacting agents (such as histones), viruses (such as adenovirus, adenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences (“MTS”) and herpes simplex virus-1 (“VP22”)), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

As stated above, coatings used with the exemplary embodiments of the present invention may comprise a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

The polymer used in the exemplary embodiments of the present invention is preferably capable of absorbing a substantial amount of drug solution. When applied as a coating on a medical device in accordance with the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2-0.3 microns and much thicker coatings, e.g., more than 10 microns, are also possible. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers.

Coatings from polymer dispersions such as polyurethane dispersions (BAYHYDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A method for selectively coating portions of a medical device comprising:

- providing a medical device, an applicator, and a spreader that is either a roller or a blade;
- applying a layer of coating having a thickness to an accessible surface of the medical device with the applicator, the applied coating masking a surface area of the medical device;
- positioning the spreader in contact with the applied coating; and
- reducing the coating thickness from a first thickness to a second thickness by spreading the coating over a surface area of the target surface larger than the surface area masked when the coating is first applied.

2. The method of claim 1, wherein the coating contains a therapeutic.

3. The method of claim 1, further comprising rotating the work piece with a machine tool.

4. The method of claim 3, wherein the machine tool is configured to move the applicator along three perpendicular axes.

5. The method of claim 3, wherein the machine tool is a lathe.

6. The method of claim 1, further comprising placing the medical device on a mandrel configured to hold the medical device and masking non-target surfaces of the medical device.

7. The method of claim 1 wherein the applicator is a micro-scale dispenser.

8. The method of claim 1 wherein the applicator has a ball-point.

9. The method of claim 1 wherein the applicator has a felt-tip.

10. A method of claim 1, further comprising partially drying the coating before positioning the spreader in contact with the coating.

11. The method of claim 1 wherein the accessible surface is an outer surface of a strut of a lattice portion of a stent.

12. The method of claim 1, wherein the spreader includes a drum rotatably positioned on a rotation point.

13. The method of claim 1, wherein the accessible surface is an exposed outer surface of a lattice strut of a stent and the spreader is sized to have about the same width as the outer surface of the strut.

14. The method of claim 1, wherein the spreader is a roller.

15. The method of claim 1, wherein the spreader is a reducing orifice.

16. The method of claim 1, wherein the spreader is a blade.

17. The method of claim 1, wherein the spreader is hand-held.

18. The method of claim 1, further comprising applying a second coating.

19. A method for coating an outer surface of a stent comprising:

providing a stent including a strut having an outer surface with a width;

providing an applicator; providing a spreader;

applying a bead of coating including a therapeutic agent, the coating having a thickness and covering a portion of the outer surface of the strut;

spreading the applied coating with the spreader, the spreader reducing the thickness of the applied coating during spreading, and spreading the coating over a larger portion of the outer surface of the strut during spreading, wherein the spreader is sized to have about the same width as the width of the outer surface of the strut.

* * * * *